(12) United States Patent
Ye et al.

(10) Patent No.: US 9,522,911 B2
(45) Date of Patent: Dec. 20, 2016

(54) CRYSTALLINE FORMS OF TRICYCLIC COMPOUND ACID SALT OR HYDRATE THEREOF, AND METHOD FOR MAKING THEREOF

(71) Applicant: Jeil Pharmaceutical Co., Ltd., Seoul (KR)

(72) Inventors: In-Hae Ye, Yongin-si (KR); Chun-Ho Park, Yongin-si (KR); Jong-Hee Choi, Suwon-si (KR); Dong-il Kang, Yongin-si (KR)

(73) Assignee: JEIL PHARMACEUTICAL CO., LTD., Seoul (KR)

( * ) Notice: Subject to any disclaimer, the term of this patent is extended or adjusted under 35 U.S.C. 154(b) by 35 days.

(21) Appl. No.: 14/338,923

(22) Filed: Jul. 23, 2014

(65) Prior Publication Data

US 2014/0350007 A1    Nov. 27, 2014

Related U.S. Application Data

(63) Continuation-in-part of application No. PCT/KR2013/000676, filed on Jan. 28, 2013.

(30) Foreign Application Priority Data

Feb. 1, 2012  (KR) .................. 10-2012-0010465

(51) Int. Cl.

| | | |
|---|---|---|
| C07D 471/04 | (2006.01) |
| C07C 53/06 | (2006.01) |
| C07C 55/10 | (2006.01) |
| C07C 55/14 | (2006.01) |
| C07C 57/145 | (2006.01) |
| C07C 57/15 | (2006.01) |
| C07C 59/245 | (2006.01) |
| C07C 59/255 | (2006.01) |
| C07C 229/24 | (2006.01) |
| C07C 307/02 | (2006.01) |
| C07C 309/04 | (2006.01) |
| C07C 309/19 | (2006.01) |
| C07C 309/29 | (2006.01) |
| C07D 239/22 | (2006.01) |

(52) U.S. Cl.
CPC ............. *C07D 471/04* (2013.01); *C07C 53/06* (2013.01); *C07C 55/10* (2013.01); *C07C 55/14* (2013.01); *C07C 57/145* (2013.01); *C07C 57/15* (2013.01); *C07C 59/245* (2013.01); *C07C 59/255* (2013.01); *C07C 229/24* (2013.01); *C07C 307/02* (2013.01); *C07C 309/04* (2013.01); *C07C 309/19* (2013.01); *C07C 309/29* (2013.01); *C07D 239/22* (2013.01)

(58) Field of Classification Search
CPC .................................................... C07D 471/04
See application file for complete search history.

(56) References Cited

U.S. PATENT DOCUMENTS

| | | | |
|---|---|---|---|
| 6,696,437 B1 | 2/2004 | Lubisch | |
| 8,815,891 B2 * | 8/2014 | Kim .................. | C07D 471/04 514/291 |
| 2004/0067949 A1 | 4/2004 | Grandel | |
| 2005/0074470 A1 | 4/2005 | Li | |
| 2011/0218193 A1* | 9/2011 | Kim .................. | C07D 471/04 514/228.2 |

FOREIGN PATENT DOCUMENTS

KR    10-2010-0053468 A    5/2010

OTHER PUBLICATIONS

Berge et al., Journal of Pharmaceutical Sciences, vol. 66, No. 1, Jan. 1977, pp. 1-19.*
Developing Solid Oral Dosage Forms: Pharmaceutical Theory & Practice, Chapter 4, Wei-Qin Tong, pp. 75-86, Mar. 10, 2009.*

* cited by examiner

*Primary Examiner* — Rebecca Anderson
(74) *Attorney, Agent, or Firm* — Lucas & Mercanti, LLP (57) ABSTRACT

The present invention relates to a novel crystalline acid salt of a tricyclic derivative or a hydrate thereof and a production method thereof. The crystalline acid salt or the hydrate thereof according to the present invention is stable with respect to humidity and stable with respect to hygroscopicity, and the quality control during manufacturing drugs is favorable. In addition, the crystalline acid salt or the hydrate thereof may be used in a pharmaceutical composition for preventing or treating neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity.

4 Claims, 3 Drawing Sheets

CRYSTALLINE FORMS OF TRICYCLIC COMPOUND ACID SALT OR HYDRATE THEREOF, AND METHOD FOR MAKING THEREOF

CROSS-REFERENCE TO RELATED APPLICATIONS

This application is a continuation-in-part of PCT/KR2013/000676, filed Jan. 28, 2013, which claims the benefit of Korean Patent Application No. 10-2012-0010465, filed Feb. 1, 2012, the contents of each of which are incorporated herein by reference.

TECHNICAL FIELD

The present disclosure relates to novel crystalline acid salts of a tricyclic derivative or a hydrate thereof, and a production method thereof.

BACKGROUND

Drugs administered orally show medicinal effects through absorption, distribution, metabolism or elimination, and the intrinsic properties of a solid state, a salt state, a specific state of drug candidates are also significant in the drug development.

Different from thermodynamically stable crystalline state, amorphous solid has a thermodynamically very unstable state. Thus, the amorphous solid has a rapid elution rate and high solubility when compared to the crystalline solid. Accordingly, even though they are the same chemical compound, different bioavailability may be obtained.

Particularly, since the arriving rate of orally administered active ingredients to the blood of a patient is influenced by the elution rate, and the elution rate of the active ingredients from the gastrointestinal fluid of the patient plays an important role in attaining treating effects, the elution rate in an aqueous solution is significant. Among the drug states, the amorphous state dissolves fast and works fast with short duration time, however the crystalline state dissolves slowly and works slowly with long duration time.

Each of the solid state (crystalline or amorphous) drug candidates has different physical and chemical properties such as solubility, stability or reproduction capability. These properties may influence the final drug administration type, the optimized producing process, and the absorption in a human body, and the discovery of the most appropriate type for the drug development from now on may decrease time and costs necessary for the development.

Substantially, the acquisition of pure crystalline state and amorphous state, or even other noncrystalline state is very favorable in the drug development. These types may impart the chemical and physical properties of drug candidates with even better properties. Thus, the formation or the identification of the states for the combination of desired treating effects may become possible, and the preparation of a drug may become relatively easy. The solid phase crystalline state has more favorable pharmacological properties, is produced easily, and has better storing stability.

For the crystalline compounds having any states such as a dissolved state, the amount of residual solvents in a final drug may be small. In addition, through the crystallization, additional purification effect may be obtained. In addition, since this state is very stable during manufacturing a drug, the handling thereof during manufacturing is favorable.

The inventors of the present application has filed a patent application with the title of "10-ethoxy-8-(morpholinomethyl)-1,2,3,4-tetrahydrobenzo[h][1,6]naphthydine-5(6H)-on dichloride and a production method thereof", represented by the following Chemical Formula, which has been registered with the Korean Patent Registration No. 10-0968175.

The 10-ethoxy-8-(morpholinomethyl)-1,2,3,4-tetrahydrobenzo[h][1,6]naphthydine-5(6H)-on dichloride is a tricyclic derivative having a poly(ADP-ribose) polymerase (PARP) inhibition activity, which may be advantageously used as an effective ingredient in a pharmaceutical composition for preventing or treating neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity.

However, for the preparation of the compound, an excessive amount of solvents is used in the case of mass production using column chromatography. Thus, mass production is difficult due to environmental problem, and much costs and time.

In addition, since 10-ethoxy-8-(morpholinomethyl)-1,2,3,4-tetrahydrobenzo[h][1,6]naphthydine-5(6H)-on dichloride anhydride absorbs humidity in the air, and the weight thereof may increase, careful handling is required. An amorphous 10-ethoxy-8-(morpholinomethyl)-1,2,3,4-tetrahydrobenzo[h][1,6]naphthydine-5(6H)-on dichloride absorbs humidity in the air fast and changes into a crystalline state unstably.

Therefore, the inventors of the present application have studied on a stable crystalline state of the 10-ethoxy-8-(morpholinomethyl)-1,2,3,4-tetrahydrobenzo[h][1,6]naphthydine-5(6H)-on dichloride to solve the above-described defects, obtained a stable crystalline state of a 10-ethoxy-8-(morpholinomethyl)-1,2,3,4-tetrahydrobenzo[h][1,6]naphthydine-5(6H)-on compound in a high yield, and suggested a separation method to complete the present invention.

SUMMARY OF INVENTION

One object of the present invention is to provide novel crystalline acid salts of a tricyclic derivative or a hydrate thereof.

Another object of the present invention is to provide a production method of the crystalline acid salt of a tricyclic derivative or a hydrate thereof.

Still another object of the present invention is to provide a pharmaceutical composition including the crystalline acid salt of a tricyclic derivative or a hydrate thereof and a pharmaceutically acceptable carrier, for preventing or treating diseases induced by PARP (poly(ADP-ribose) polymerase) overactivity.

In order to achieve the objects, the present invention provides novel crystalline acid salts of a tricyclic derivative or a hydrate thereof represented by the following Chemical Formula 1:

[Chemical Formula 1]

where n, m and X are the same as defined in the present specification.

The present invention also provides a production method of the crystalline acid salt of a tricyclic derivative or a hydrate thereof, including adding an acid in a tricyclic derivative of following Chemical Formula 1A in water or an organic solvent, performing a reaction, completing the reaction, and first recrystallizing using an organic solvent (Step 1); and second recrystallizing the solid obtained in Step 1 using water and an organic solvent (Step 2), as shown in following Reaction Formula 1:

[Reaction Formula 1]

wherein n, m and X are the same as defined in the present specification.

Furthermore, the present invention provides a pharmaceutical composition including the crystalline acid salt of a tricyclic derivative or a hydrate thereof and a pharmaceutically acceptable carrier, for preventing and treating diseases induced by PARP overactivity.

The crystalline acid salt or the hydrate thereof according to the present invention is stable with respect to humidity and stable with respect to hygroscopicity, and the quality control during manufacturing drugs is favorable. In addition, the crystalline acid salt or the hydrate thereof may be used in a pharmaceutical composition for preventing or treating neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity.

DETAILED DESCRIPTION OF INVENTION

Hereinafter, the present invention will be described in detail.

The present invention provides novel crystalline acid salts of a tricyclic derivative or a hydrate thereof represented by the following Chemical Formula 1.

[Chemical Formula 1]

where n or m is an integer from 0 to 3; and

X is a pharmaceutically acceptable inorganic acid or an organic acid.

Preferably, in the above Chemical Formula 1, n or m is an integer from 0 to 3; and

X is one selected from the group consisting of hydrochloric acid, benzenesulfonic acid, maleic acid, dimethanesulfonic acid, bis[(7,7-dimethyl-2-oxobicyclo[2,2,1]heptane-1-yl)methanesulfonic acid], tartaric acid, 2,6-dioxo-1,2,3,6-tetrahydropyrimidine-4-carboxylic acid, adipic acid, dinitric acid, fumaric acid, (S)-2-amino succinic acid, 2-hydroxypropane-1,2,3-tricarboxylic acid, cyclohexylsulphamic acid, sulfuric acid, succinic acid, formic acid, glutamic acid and diphosphoric acid.

More preferably, the novel crystalline acid salt of a tricyclic derivative or a hydrate thereof represented by the above Chemical Formula 1 is one selected from the group consisting of:

(1) 10-ethoxy-8-(morpholinomethyl)-1,2,3,4-tetrahydrobenzo[h][1,6]naphthyridine-5(6H)-on dichloride dihydrate;
(2) 10-ethoxy-8-(morpholinomethyl)-1,2,3,4-tetrahydrobenzo[h][1,6]naphthyridine-5(6H)-on benzenesulfonate;
(3) 10-ethoxy-8-(morpholinomethyl)-1,2,3,4-tetrahydrobenzo[h][1,6]naphthyridine-5(6H)-on maleate;
(4) 10-ethoxy-8-(morpholinomethyl)-1,2,3,4-[h][1,6]naphthyridine-5(6H)-on dimethanesulfonate;
(5) 10-ethoxy-8-(morpholinomethyl)-1,2,3,4-tetrahydrobenzo[h][1,6]naphthyridine-5(6H)-on bis[(7,7-dimethyl-2-oxobicyclo[2,2,1]heptane-1-yl)methanesulfonate];
(6) 10-ethoxy-8-(morpholinomethyl)-1,2,3,4-tetrahydrobenzo[h][1,6]naphthyridine-5(6H)-on tartarate;
(7) 10-ethoxy-8-(morpholinomethyl)-1,2,3,4-tetrahydrobenzo[h][1,6]naphthyridine-5(6H)-on 2,6-dioxo-1,2,3,6-tetrahydropyrimidine-4-carboxylate;
(8) 10-ethoxy-8-(morpholinomethyl)-1,2,3,4-tetrahydrobenzo[h][1,6]naphthyridine-5(6H)-on adipate;
(9) 10-ethoxy-8-(morpholinomethyl)-1,2,3,4-tetrahydrobenzo[h][1,6]naphthyridine-5(6H)-on nitrite;
(10) 10-ethoxy-8-(morpholinomethyl)-1,2,3,4-tetrahydrobenzo[h][1,6]naphthyridine-5(6H)-on fumarate;
(11) 10-ethoxy-8-(morpholinomethyl)-1,2,3,4-tetrahydrobenzo[h][1,6]naphthyridine-5(6H)-on (S)-2-amino succinate;
(12) 10-ethoxy-8-(morpholinomethyl)-1,2,3,4-tetrahydrobenzo[h][1,6]naphthyridine-5(6H)-on 2-hydroxypropane-1,2,3-tricarboxylate;
(13) 10-ethoxy-8-(morpholinomethyl)-1,2,3,4-tetrahydrobenzo[h][1,6]naphthyridine-5(6H)-on cyclohexylsulphamate;
(14) 10-ethoxy-8-(morpholinomethyl)-1,2,3,4-tetrahydrobenzo[h][1,6]naphthyridine-5(6H)-on sulfate;
(15) 10-ethoxy-8-(morpholinomethyl)-1,2,3,4-tetrahydrobenzo[h][1,6]naphthyridine-5(6H)-on succinate;
(16) 10-ethoxy-8-(morpholinomethyl)-1,2,3,4-tetrahydrobenzo[h][1,6]naphthyridine-5(6H)-on formate;
(17) 10-ethoxy-8-(morpholinomethyl)-1,2,3,4-tetrahydrobenzo[h][1,6]naphthyridine-5(6H)-on glutamate; and
(18) 10-ethoxy-8-(morpholinomethyl)-1,2,3,4-tetrahydrobenzo[h][1,6]naphthyridine-5(6H)-on diphosphate.

Most preferably, the novel crystalline acid salt of a tricyclic derivative or a hydrate thereof of the above Chemical Formula 1 is 10-ethoxy-8-(morpholinomethyl)-1,2,3,4-tetrahydrobenzo[h][1,6]naphthyridine-5(6H)-on dichloride dihydrate represented by the following Chemical Formula 2.

[Chemical Formula 2]

The crystalline dichloride dihydrate of Chemical Formula 2 has 2θ values of X-ray diffraction peaks of 6.59°, 7.74°, 8.42°, 10.15°, 12.52°, 23.30° and 25.30° in an X-ray diffraction pattern of Cu target radiation.

In addition, the present invention provides a production method of the crystalline acid salt of a tricyclic derivative or a hydrate thereof represented by the above Chemical Formula 1.

Particularly, the production method includes:

adding an acid in a tricyclic derivative of the following Chemical Formula 1A in water or an organic solvent, performing a reaction, completing the reaction, and first recrystallizing using an organic solvent (Step 1); and second recrystallizing the solid obtained in Step 1 using water and an organic solvent (Step 2), as shown in following Reaction Formula 1.

[Reaction Formula 1]

where n, m and X are the same as defined in the above Chemical Formula 1.

The above Step 1 is a step for obtaining a target compound by dissolving a tricyclic derivative of the above Chemical Formula 1A in an organic solvent and adding an acid thereto.

In this case, the organic solvent may be a $C_1$-$C_4$ alcohol, and may preferably be methanol or ethanol.

In addition, the acid may be a pharmaceutically acceptable inorganic acid or an organic acid, and may be one selected from the group consisting of hydrochloric acid, benzenesulfonic acid, maleic acid, dimethanesulfonic acid, bis[(7,7-dimethyl-2-oxobicyclo[2,2,1]heptane-1-yl)methanesulfonic acid], tartaric acid, 2,6-dioxo-1,2,3,6-tetrahydropyrimidine-4-carboxylic acid, adipic acid, dinitric acid, fumaric acid, (S)-2-amino succinic acid, 2-hydroxypropane-1,2,3-tricarboxylic acid, cyclohexylsulphamic acid, sulfuric acid, succinic acid, formic acid, glutamic acid and diphosphoric acid.

Further, the organic solvent used in the first recrystallization in the above Step 1 means a solvent not dissolving the compound of the present invention and may be at least one selected from the group consisting of acetone, hexane, heptane, toluene, ethyl acetate, dichloromethane, tetrahydrofuran and chloroform. Preferably, a mixture of ethanol and ethyl acetate may be used.

In this case, the addition ratio of the ethanol and the ethyl acetate may be 1:8-10. In the case that the addition ratio deviates from the above range, the formation of the target compound as a solid state may be difficult.

In addition, the above Step 2 is a second recrystallization step by adding water and an organic solvent in the solid obtained in the above Step 1. After dissolving the solid obtained in the above Step 1, an anti-solvent is added, followed by stirring or leaving to obtain precipitation.

In this case, the organic solvent used means a solvent in which the compound of the present invention is insoluble, that is, an anti-solvent, and may be one selected from the group consisting of acetone, hexane, heptane, toluene, ethyl acetate, dichloromethane, tetrahydrofuran and chloroform. Preferably, the acetone may be used.

The addition ratio of the water and the acetone may be 1:8-10. In the case that the addition ratio deviates from the above range, the formation of the target compound as a solid state may be difficult.

Further, the present invention provides a pharmaceutical composition including the crystalline acid salt of a tricyclic derivative or a hydrate thereof represented by the above Chemical Formula 1 and a pharmaceutically acceptable carrier, for preventing and treating diseases induced by PARP overactivity.

The crystalline acid salt or the hydrate thereof according to the present invention is stable to humidity and stable with respect to hygroscopicity, and the quality control during manufacturing drugs is favorable (See Experimental Examples 1 and 2). In addition, since the tricyclic derivative has good treating effects on neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity (Korean Publication Patent No. 2010-0053468), the tricyclic derivative may be used as a pharmaceutical composition for preventing or treating the diseases induced by PARP overactivity.

In the case that the composition of the present invention is used as medicines, a pharmaceutical composition containing the tricyclic crystalline acid salt or a hydrate thereof as an effective ingredient may be formulated as diverse oral or parenteral administration types for clinical administration, without limitation.

The formulation for oral administration may include a tablet, a pellet, a hard/soft capsule, liquid formulation, suspension, emulsion, syrup, granule, elixirs, a troche, etc. The formulation includes a diluent (for example, lactose, dextrose, sucrose, mannitol, sorbitol, cellulose and/or glycine) and a slip modifier (for example, silica, talc, stearic acid and a magnesium or calcium salt thereof, and/or polyethylene glycol) other than the effective ingredients. The formulation may contain a binding agent such as magnesium aluminum silicate, starch paste, gelatin, methyl cellulose, sodium carboxymethyl cellulose and/or polyvinyl pyrrolidine, and may contain starch, agar, a disintegration agent such as alginic acid or a sodium salt thereof, or a boiling mixture and/or an absorbent, a coloring agent, a flavoring agent and a sweetening agent as occasion demands.

The pharmaceutical composition including the tricyclic crystalline acid salt or the hydrate thereof as an effective ingredient may be parenterally administered, and parenteral administration may include a hypodermic injection, an intravenous injection, or an intrathoracic injection.

For the formulation for the parenteral administration, the tricyclic crystalline acid salt or the hydrate thereof is mixed with a stabilizer or a buffer agent in water to produce a liquid or a suspension, and an administration type of an ample or a vial unit may be manufactured. The composition may be sterilized and/or may contain an antiseptic, a stabilizer, a water-dispersible powder or an emulsion promoter, an adjuvant such as a salt for controlling osmotic pressure and/or a buffer agent, and other useful materials for treatment. The formulation may be obtained by a common method including mixing, granulation or coating.

The dosage of the pharmaceutical composition containing the tricyclic crystalline acid salt or the hydrate thereof as an effective ingredient in a human body is dependent on the age, weight, sex, administration type, physical conditions and degree of diseases of a patient. Preferably, the composition may be orally or parenterally administered for several times a day, preferably 1 to 3 times a day with a constant time interval by the amount of 0.01 to 200 mg/kg/day according to the decision of a doctor or a pharmacist.

EXAMPLES

Hereinafter, the present invention will be explained in detail referring to examples and comparative examples.

However, the examples and the comparative examples are illustrative, and the present invention should not be construed as limited to the examples and the comparative examples set forth herein.

Example 1

Preparation of 10-ethoxy-8-(morpholinomethyl)-1,2,3,4-tetrahydrobenzo[h][1,6]naphthyridine-5(6H)-on dichloride dihydrate Step 1: Preparation of methyl 3-hydroxy-5-nitrobenzoate In 3-hydroxy-5-nitrobenzoic acid (5.9 kg, 32.2 mol), methanol (60 L) was added, and sulfuric acid (375 ml, catalytic amount) was slowly added thereto, followed by refluxing and stirring at 80° C. for 18 hours. After completing the reaction, the reactant was cooled to room temperature. Purified water (50 L) was added thereto, and methanol was distilled off under a reduced pressure. The solid thus produced was stirred at 10° C. for 1 hour and filtered. The filtrant was washed with purified water, and dried at 60° C. to obtain the title compound (5.52 kg, yield: 87%, yellow solid).

$^1$H-NMR (400 MHz, DMSO-d$^6$) δ 10.91 (s, 1H), 8.04 (s, 1H), 7.74 (s, 1H), 7.66 (s, 1H), 3.88 (s, 3H)

Step 2: Preparation of methyl 3-ethoxy-5-nitrobenzoate

In the compound prepared in Step 1 (5.52 kg, 28.0 mmol), acetonitrile (36 L) was added, and ethyl iodide (6.1 kg, 39.2 mol) and potassium carbonate (5.8 kg, 42.0 mol) were added thereto, followed by refluxing and stirring at 95° C. for 18 hours. After completing the reaction, the reactant was cooled to room temperature. Purified water (36 L) was added thereto, and acetonitrile was distilled off under a reduced pressure. The solid thus produced was filtered, washed with purified water and dried at 60° C. to obtain the title compound (6.1 kg, yield: 96.9%, yellow solid).

$^1$H-NMR (400 MHz, DMSO-d$^6$); δ 8.18 (s, 1H), 7.93 (s, 1H), 7.78 (s, 1H), 4.21 (q, J=6.6 Hz, 2H), 3.91 (s, 3H), 1.37 (t, J=6.6 Hz, 3H)

Step 3: Preparation of methyl 3-amino-5-ethoxybenzoate

In the compound prepared in Step 2 (6.1 kg, 27.1 mol), methanol (54 L) and purified water (54 L) were added, and 10%-palladium/carbon (6.1 kg, 10% wt/wt) was added thereto, followed by stirring under hydrogen gas conditions at 4 atm for 2.5 hours at room temperature. After securing the completion of the reaction, acetone (54 L) was added, and filtering was performed to remove 10%-palladium/carbon. Methanol and acetone were distilled off under a reduced pressure. The solid thus produced was filtered and washed with purified water to obtain the title compound (4.88 kg, yield: 92.2%, yellow solid).

$^1$H-NMR (400 MHz, CDCl$_3$) δ 6.95 (s, 2H), 6.39 (s, 1H), 4.01 (q, J=6.8 Hz, 2H), 3.87 (s, 3H), 3.76 (s, 2H), 1.38 (t, J=6.8 Hz, 3H)

Step 4: Preparation of methyl 3-(2-chloronicotineamido)-5-ethoxybenzoate In the compound prepared in Step 3 (4.88 kg, 25.0 mol), dichloromethane (60 L) was added, and 2-chloronicotinic acid (5.5 kg, 35.0 mol), EDC.HCl (6.7 kg, 35 mol) and hydroxybenzotriazole (1.0 kg, 7.5 mol) were added thereto, followed by stirring at room temperature for 2 hours. After securing the completion of the reaction, potassium carbonate (1.0 kg) and purified water (30 L) were added, and an organic layer was distilled under a reduced pressure. In the slurry thus produced, ethyl acetate (5 L) and n-hexane (50 L) were added and stirred. The solid thus obtained was filtered and dried to obtain the title compound (8.98 kg, yield: q. yield, off-white solid).

$^1$H-NMR (400 MHz, CDCl$_3$) δ 8.53 (s, 1H), 8.49 (d, J=4.8 Hz, 1H), 8.14 (d, J=7.6 Hz, 1H), 7.78 (s, 1H), 7.66 (s, 1H), 7.40-7.37 (m, 2H), 4.33 (qt, J=7.6 Hz, 2H), 3.88 (s, 3H), 1.38 (t, J=7.6 Hz, 3H)

Step 5: Preparation of methyl 3-(2-chloro-N-(methoxymethyl)nicotineamido)-5-ethoxybenzoate In the compound prepared in Step 4 (8.98 kg, 25.0 mol), dichloromethane (90 L) was added and dissolved, and methoxymethyl chloride (5.03 kg, 50.0 mol) and tetrabutylammonium bromide (3.2 kg, 10.0 mol) were added thereto. The reaction mixture was cooled to 10° C., and sodium hydroxide (4.0 kg, 10.0 mol) dissolved in purified water (9 L) was added drop by drop, followed by vigorous stirring at room temperature for 4 hours. After securing the completion of the reaction, purified water (30 L) was added, and an organic layer was distilled under a reduced pressure. In the slurry thus produced, ethyl acetate (50 L) was added and dissolved, and the resultant was washed with purified water (40 L) for 6 times, distilled under a reduced pressure and vacuum dried to obtain the title compound (9.0 kg, yield: 95.0%, yellow solid).

$^1$H-NMR (400 MHz, DMSO-$d^6$) δ 8.24 (d, 1H, J=2.4 Hz), 7.93 (d, 1H, J=4.4 Hz), 7.41 (s, 1H), 7.30-7.29 (m, 1H), 7.21 (s, 1H), 7.15 (s, 1H), 5.17 (s, 2H), 3.94 (q, 2H, J=6.8 Hz), 3.77 (s, 3H), 3.41 (s, 3H), 1.23 (t, 3H, J=6.8 Hz)

Step 6: Preparation of methyl 10-ethoxy-6-(methoxymethyl)-5-oxo-5,6-dihydrobenzo[h][1,6]naphthyridine-8-carboxylate In the compound prepared in Step 5 (11.4 kg, 30.0 mol), N,N-dimethylformamide (54 L) was added, and palladium acetate (1.84 kg, 7.52 mol), tributyl phosphine (6.1 kg, 30.0 mol) and potassium carbonate (8.3 kg, 60.0 mol) were added thereto, followed by stirring at 130° C. for 2 hours. After securing the completion of the reaction, the reactant was cooled, and purified water (108 L) was added. The solid thus produced was filtered, washed with purified water and dried at 60° C. to obtain the title compound (6.88 kg, yield: 67.0%, black solid).

$^1$H-NMR (400 MHz, CDCl$_3$) δ 9.11-9.10 (m, 1H), 8.84 (td, J=2.0 Hz, 8.0 Hz, 1H), 7.97 (s, 1H), 7.60 (s, 1H), 7.53-7.50 (m, 1H), 5.85 (s, 2H), 4.34 (q, J=6.8 Hz, 2H), 3.98 (s, 3H), 3.49 (s, 3H), 1.60 (t, J=6.8 Hz, 3H)

Step 7: Preparation of methyl 10-ethoxy-6-(methoxymethyl)-5-oxo-1,2,3,4,5,6-hexahydrobenzo[h][1,6]naphthyridine-8-carboxylate In the compound prepared in Step 6 (6.88 kg, 27.1 mol), tetrahydrofuran (54 L) and purified water (54 L) were added, and 10%-palladium/carbon (13.8 kg, 20% wt/wt) was added thereto, followed by stirring in hydrogen gas conditions at 4 atm for 4.5 hours at room temperature. After securing the completion of the reaction, dichloromethane (54 L) was added. Filtering was performed to remove 10%-palladium/carbon, and an organic layer was distilled under a reduced pressure. In the slurry thus produced, n-hexane (50 L) was added and stirred for 1 hour. The solid thus produced was filtered and dried to obtain the title compound (5.01 kg, yield: 72.2%, off-white solid).

$^1$H-NMR (400 MHz, CDCl$_3$) δ 7.85 (s, 1H), 7.63 (s, 1H), 7.29 (s, 1H), 5.73 (s, 2H), 4.26 (q, J=7.2 Hz, 2H), 3.94 (s, 3H), 3.42 (s, 3H), 3.42-3.37 (m, 2H), 2.69 (t, J=6.0 Hz, 2H), 1.93-1.90 (m, 2H), 1.53 (t, J=7.2 Hz, 3H)

Step 8: Preparation of 10-ethoxy-8-(hydroxymethyl)-6-(methoxymethyl)-1,2,3,4-tetrahydrobenzo[h][1,6]naphthyridine-5-(6H)-on In the compound prepared in Step 7 (500 g, 1.44 mol), tetrahydrofuran (4 L) was added, and lithiumaluminum hydride (50.0 g, 1.34 mol) was slowly added at 10° C., followed by stirring at room temperature for 1 hour. After securing the completion of the reaction, purified water (50 ml), 15% aqueous sodium hydroxide solution (50 ml) and purified water (150 ml) were slowly added one by one, followed by stirring at room temperature for 2 hours. The slurry thus produced was filtered, and the filtrate was concentrated under a reduced pressure. In the solid thus produced, ethyl acetate (2.0 L) was added and stirred for 1 hour. Filtering and drying were performed to obtain the title compound (361 g, yield: 78.7%, off-white solid).

$^1$H-NMR (400 MHz, CDCl$_3$) δ 7.63 (s, 1H), 7.00 (s, 1H), 6.73 (s, 1H), 5.55 (s, 2H), 4.69 (s, 2H), 4.19 (q, J=7.2 Hz, 2H), 3.36-3.35 (m, 2H), 3.36 (s, 3H), 2.65 (t, J=6.0 Hz, 2H), 1.91-1.88 (m, 2H), 1.51 (t, J=7.2 Hz, 3H)

Step 9: Preparation of 8-(chloromethyl)-10-ethoxy-6-(methoxymethyl)-1,2,3,4-tetrahydrobenzo[h][1,6]naphthyridine-5-(6H)-on In the compound prepared in Step 8 (310.1 g, 0.97 mol), dichloromethane (1.5 L) was added, and thionyl chloride (106.5 ml, 1.46 mol) was slowly added at 0° C., followed by refluxing and stirring at 50° C. for 2 hours. After securing the completion of the reaction, purified water (500 ml) was added, and neutralization was performed using an aqueous sodium bicarbonate solution. An organic layer was concentrated under a reduced pressure. The solid thus produced was recrystallized using ethyl acetate (0.5 L) and n-hexane (1.0 L) to obtain the title compound (305.4 g, yield: 93.1%, off-white solid).

$^1$H-NMR (400 MHz, CDCl$_3$) δ 7.59 (s, 1H), 7.14 (s, 1H), 6.69 (s, 1H), 5.67 (s, 2H), 4.59 (s, 2H), 4.20 (q, 2H, J=6.8 Hz), 3.40 (s, 3H), 3.40-3.35 (m, 2H), 2.66 (t, 2H, J=6.0 Hz), 1.92-1.86 (m, 2H), 1.53 (t, 3H, J=6.8 Hz)

Step 10: Preparation of 10-ethoxy-6-(methoxymethyl)-8-(morpholinomethyl)-1,2,3,4-tetrahydrobenzo[h][1,6]naphthyridine-5-(6H)-on

In the compound prepared in Step 9 (305.4 g, 0.907 mol), methanol (3.0 L) and morpholine (395 ml, 4.53 mol) were added one by one, followed by refluxing and stirring at 80° C. for 18 hours. After securing the completion of the reaction, purified water (3.0 L) was added, and an organic layer was concentrated under a reduced pressure. The solid thus produced was recrystallized using ethyl acetate (1.0 L) and n-hexane (2.0 L) to obtain the title compound (326.9 g, yield: 96.5%, off-white solid).

$^1$H-NMR (400 MHz, DMSO) δ 7.61 (s, 1H), 7.08 (s, 1H), 6.72 (s, 1H), 5.68 (s, 2H), 4.19 (q, 2H, J=6.8 Hz), 3.72-3.69 (m, 4H), 3.51 (s, 2H), 3.40 (s, 3H), 3.40-3.35 (m, 2H), 2.66 (t, 2H, J=6.0 Hz), 2.45 (m, 4H), 1.90-1.87 (m, 2H), 1.52 (t, 3H, J=6.8 Hz)

Step 11: Preparation of 10-ethoxy-8-(morpholinomethyl)-1,2,3,4-tetrahydrobenzo[h][1,6]naphthyridine-5(6H)-on dichloride dihydrate -continued In the compound prepared in Step 10 (326.9 g, 0.875 mol), ethanol (2.3 L) and c-hydrochloric acid (230 ml) were added, followed by refluxing and stirring at 90° C. for 3 hours. After securing the completion of the reaction, the reaction mixture was concentrated under a reduced pressure and recrystallized in ethanol (100 ml) and ethyl acetate (900 ml). The solid thus produced was recrystallized using water (1.0 L) and acetone (8.0 L) to obtain the title compound (351 g, yield: 88.7%, moisture content: 8.5%, white solid).

$^1$H-NMR (400 MHz, DMSO-$d^6$) δ 12.21 (s, 1H), 12.13 (s, 1H), 7.55 (s, 1H), 7.11 (s, 1H), 4.39-4.34 (m, 4H), 3.91-3.90 (m, 4H), 3.44-3.41 (m, 2H), 3.19-3.13 (m, 4H), 2.50 (t, 2H, J=6.0 Hz), 1.80-1.77 (m, 2H), 1.44 (t, 3H, J=6.8 Hz)

Example 2

Preparation of 10-ethoxy-8-(morpholinomethyl)-1,2,3,4-tetrahydrobenzo[h][1,6]naphthyridine-5(6H)-on benzenesulfonate The same procedure was performed as described in Example 1, except for using benzenesulfonic acid instead of c-hydrochloric acid in Step 10 to obtain the title compound (716 mg, 98%).

$^1$H-NMR (400 MHz, DMSO-$d^6$) δ 11.34 (s, 1H), 9.87 (Br, 1H), 7.61-7.59 (m, 2H), 7.35-7.30 (m, 3H), 6.92 (s, 1H), 6.87 (s, 1H), 4.34 (Br, 2H), 4.23 (q, J=3.4 Hz, 2H), 3.98-3.95 (m, 2H), 3.63 (t, J=12.0 Hz, 2H), 3.36 (Br, 2H), 3.28 (d, J=6.2 Hz, 2H), 3.15-3.13 (m, 2H), 2.48-2.45 (m, 2H), 1.78-1.75 (m, 2H), 1.44 (t, J=6.8 Hz, 3H)

Example 3

Preparation of 10-ethoxy-8-(morpholinomethyl)-1,2,3,4-tetrahydrobenzo[h][1,6]naphthyridine-5(6H)-on maleate The same procedure was performed as described in Example 1, except for using maleic acid instead of c-hydrochloric acid in Step 10 to obtain the title compound (569 mg, 85%).

$^1$H-NMR (400 MHz, DMSO-$d^6$) δ 10.92 (Br, 1H), 7.38 (s, 1H), 6.83 (s, 1H), 6.72 (s, 1H), 6.10 (s, 1H), 4.21 (q, J=3.6 Hz, 2H), 3.70 (Br, 4H), 3.32 (Br, 6H), 2.94 (Br, 2H), 2.43 (t, J=6.4 Hz, 2H), 1.75 (t, J=5.6 Hz, 2H), 1.05 (t, J=7.2 Hz, 3H)

Example 4

Preparation of 10-ethoxy-8-(morpholinomethyl)-1,2,3,4-tetrahydrobenzo[h][1,6]naphthyridine-5(6H)-on dimethanesulfonate The same procedure was performed as described in Example 1, except for using dimethanesulfonic acid instead of c-hydrochloric acid in Step 10 to obtain the title compound (760 mg, 97%).

$^1$H-NMR (400 MHz, DMSO-$d^6$) δ 11.69 (s, 1H), 10.01 (s, 1H), 7.88-7.85 (Br, 2H), 6.98 (s, 1H), 6.97 (s, 1H), 4.36 (s, 2H), 4.29 (q, J=6.8 Hz, 2H), 3.96 (m, 2H), 3.65 (m, 2H), 3.38 (m, 2H), 3.27 (m, 2H), 3.15 (m, 2H), 2.48 (m, 2H), 2.38 (s, 6H), 1.77 (m, 2H), 1.45 (t, J=6.8 Hz, 3H)

Example 5

Preparation of 10-ethoxy-8-(morpholinomethyl)-1,2,3,4-tetrahydrobenzo[h][1,6]naphthyridine-5(6H)-on bis[(7,7-dimethyl-2-oxobicyclo[2,2,1]heptane-1-yl)methanesulfonate]

The same procedure was performed as described in Example 1, except for using bis[(7,7-dimethyl-2-oxobicyclo[2,2,1]heptane-1-yl)methanesulfonic acid instead of c-hydrochloric acid in Step 10 to obtain the title compound (900 mg, 77%).

$^1$H-NMR (400 MHz, DMSO-d$^6$) δ 11.60 (s, 1H), 9.98 (s, 1H), 7.82-7.23 (Br, 2H), 6.95 (m, 2H), 4.33 (s, 2H), 4.27 (q, J=6.8 Hz, 2H), 3.94 (m, 2H), 3.65 (m, 2H), 3.36 (m, 2H), 3.25 (m, 2H), 3.14 (m, 2H), 2.90 (s, 1H), 2.87 (s, 1H), 2.62 (m, 2H), 2.45 (m, 2H), 2.42 (s, 1H), 2.38 (s, 1H), 2.24 (m, 1H), 2.19 (m, 1H), 1.92 (t, J=4.4 Hz, 2H), 1.85-1.74 (m, 6H), 1.43 (t, J=7.2 Hz, 3H), 1.31-1.22 (m, 4H), 1.01 (s, 6H), 0.71 (s, 6H)

Example 6

Preparation of 10-ethoxy-8-(morpholinomethyl)-1,2,3,4-tetrahydrobenzo[h][1,6]naphthyridine-5(6H)-on tartarate The same procedure was performed as described in Example 1, except for using tartaric acid instead of c-hydrochloric acid in Step 10 to obtain the title compound (640 mg, 89%).

$^1$H-NMR (400 MHz, DMSO-d$^6$) δ 10.69 (s, 1H), 7.36 (s, 1H), 6.76 (s, 1H), 6.60 (s, 1H), 4.29 (s, 2H), 4.16 (q, J=6.8 Hz, 2H), 3.58 (m, 4H), 3.44 (s, 2H), 3.31 (m, 2H), 2.41-2.38 (m, 6H), 1.74 (m, 2H), 1.40 (t, J=6.8 Hz, 3H)

Example 7

Preparation of 10-ethoxy-8-(morpholinomethyl)-1,2,3,4-tetrahydrobenzo[h][1,6]naphthyridine-5(6H)-on 2,6-dioxo-1,2,3,6-tetrahydropyrimidine-4-carboxylate The same procedure was performed as described in Example 1, except for using 2,6-dioxo-1,2,3,6-tetrahydropyrimidine-4-carboxylic acid instead of c-hydrochloric acid in Step 10 to obtain the title compound (640 mg, 88%).

$^1$H-NMR (400 MHz, DMSO-d$^6$) δ 11.19 (s, 1H), 10.85 (s, 1H), 10.42 (s, 1H), 7.36 (s, 1H), 6.81 (s, 1H), 6.71 (s, 1H), 5.89 (s, 1H), 4.16 (q, J=6.8 Hz, 2H), 3.81 (s, 2H), 3.68 (m, 4H), 3.31 (m, 2H), 2.72 (m, 4H), 2.42 (t, J=6.0 Hz, 2H), 1.74 (m, 2H), 1.40 (t, J=6.8 Hz, 3H)

Example 8

Preparation of 10-ethoxy-8-(morpholinomethyl)-1,2,3,4-tetrahydrobenzo[h][1,6]naphthyridine-5(6H)-on adipate The same procedure was performed as described in Example 1, except for using adipic acid instead of c-hydrochloric acid in Step 10 to obtain the title compound (400 mg, 56%).

$^1$H-NMR (400 MHz, DMSO-d$^6$) δ 12.04 (s, 1H), 10.69 (s, 1H), 7.36 (s, 1H), 6.76 (s, 1H), 6.59 (s, 1H), 4.17 (q, J=3.4 Hz, 2H), 3.58 (Br, 4H), 3.41 (Br, 2H), 3.31 (Br, 2H), 2.42 (t, J=6.0 Hz, 2H), 2.35 (Br, 4H), 1.74 (Br, 2H), 1.49 (Br, 4H), 1.41 (t, J=7.2 Hz, 3H)

Example 9

Preparation of 10-ethoxy-8-(morpholinomethyl)-1,2,3,4-tetrahydrobenzo[h][1,6]naphthyridine-5(6H)-on nitrite The same procedure was performed as described in Example 1, except for using dinitric acid instead of c-hydrochloric acid in Step 10 to obtain the title compound (638 mg, 96%).

$^1$H-NMR (400 MHz, DMSO-d$^6$) δ 11.61 (s, 1H), 9.91 (Br, 1H), 7.85 (Br, 1H), 6.96 (s, 1H), 6.89 (s, 1H), 4.36-4.35 (m, 2H), 4.27 (q, J=3.4 Hz, 2H), 3.97 (d, J=5.6 Hz, 2H), 3.61 (t, J=11.6 Hz, 2H), 3.41-3.37 (m, 2H), 3.28 (d, J=6.0 Hz, 2H), 3.16-3.13 (m, 2H), 2.50-2.48 (m, 2H), 1.79-1.76 (m, 2H), 1.45 (t, J=7.2 Hz, 3H)

Example 10

Preparation of 10-ethoxy-8-(morpholinomethyl)-1,2,3,4-tetrahydrobenzo[h][1,6]naphthyridine-5(6H)-on fumarate The same procedure was performed as described in Example 1, except for using fumaric acid instead of c-hydrochloric acid in Step 10 to obtain the title compound (426 mg, 64%).

$^1$H-NMR (400 MHz, DMSO-d$^6$) δ 13.15 (Br, 1H), 10.68 (s, 1H), 7.34 (s, 1H), 6.74 (s, 1H), 6.60-6.58 (m, 3H), 4.14 (q, J=3.8 Hz, 2H), 3.56 (Br, 4H), 3.41 (s, 2H), 3.29 (Br, 2H), 2.41-2.35 (m, 6H), 1.73-1.71 (m, 2H), 1.38 (t, J=6.8 Hz, 3H)

Example 11

Preparation of 10-ethoxy-8-(morpholinomethyl)-1,2,3,4-tetrahydrobenzo[h][1,6]naphthyridine-5(6H)-on (S)-2-amino succinate The same procedure was performed as described in Example 1, except for using (S)-2-amino succinic acid instead of c-hydrochloric acid in Step 10 to obtain the title compound (620 mg, 89%).

$^1$H-NMR (400 MHz, DMSO-d$^6$) δ 10.68 (s, 1H), 7.35 (s, 1H), 6.75 (s, 1H), 6.58 (s, 1H), 4.16 (q, J=6.8 Hz, 2H), 3.77 (m, 1H), 3.57 (m, 4H), 3.40 (s, 2H), 3.30 (m, 2H), 2.72 (m, 1H), 2.43-2.39 (m, 3H), 2.34 (m, 4H), 1.74 (m, 2H), 1.40 (t, J=6.8 Hz, 3H).

Example 12

Preparation of 10-ethoxy-8-(morpholinomethyl)-1,2,3,4-tetrahydrobenzo[h][1,6]naphthyridine-5(6H)-on 2-hydroxypropane-1,2,3-tricarboxylate The same procedure was performed as described in Example 1, except for using 2-hydroxypropane-1,2,3-tricarboxylic acid instead of c-hydrochloric acid in Step 10 to obtain the title compound (665 mg, 85%).

$^1$H-NMR (400 MHz, DMSO-d$^6$) δ 10.75 (s, 1H), 7.37 (s, 1H), 6.78 (s, 1H), 6.62 (s, 1H), 4.17 (q, J=3.8 Hz, 2H), 3.61 (Br, 4H), 3.53 (s, 2H), 3.31 (Br, 2H), 2.68 (dd, J=12.4 Hz, J=7.6 Hz, 4H), 2.50-2.40 (m, 6H), 1.76-1.73 (m, 2H), 1.41 (t, J=6.0 Hz, 3H)

Example 13

Preparation of 10-ethoxy-8-(morpholinomethyl)-1,2,3,4-tetrahydrobenzo[h][1,6]naphthyridine-5(6H)-on cyclohexylsulphamate The same procedure was performed as described in Example 1, except for using cyclohexylsulphamic acid instead of c-hydrochloric acid in Step 10 to obtain the title compound (453 mg, 75%).

$^1$H-NMR (400 MHz, DMSO-d$^6$) δ 10.76 (br s, 1H), 7.37 (s, 1H), 6.78 (s, 1H), 6.64 (s, 1H), 4.21~4.16 (m, 2H), 3.34~3.31 (m, 5H), 3.09 (br s, 1H), 2.43~2.40 (m, 4H), 2.08~2.06 (m, 2H), 1.76~1.69 (m, 4H), 1.55~1.52 (m, 2H), 1.42 (t, J=6.8 Hz, 3H), 1.27~1.07 (m, 6H)

Example 14

Preparation of 10-ethoxy-8-(morpholinomethyl)-1,2,3,4-tetrahydrobenzo[h][1,6]naphthyridine-5(6H)-on sulfate The same procedure was performed as described in Example 1, except for using sulfuric acid instead of c-hydrochloric acid in Step 10 to obtain the title compound (511 mg, 99%).

$^1$H-NMR (400 MHz, DMSO-d$^6$) δ 11.07 (s, 1H), 9.83 (br s, 1H), 7.40 (br s, 1H), 6.86 (s, H), 6.79 (s, 1H), 4.30~4.26 (m, 2H), 4.24~4.20 (m, 2H), 3.98~3.94 (m, 4H), 3.61 (t, J=11.9 Hz, 2H), 3.32~3.25 (m, 4H), 3.19~3.13 (m, 2H), 1.75~1.62 (m, 2H), 1.45 (t, J=6.9 Hz, 3H)

Example 15

Preparation of 10-ethoxy-8-(morpholinomethyl)-1,2,3,4-tetrahydrobenzo[h][1,6]naphthyridine-5(6H)-on succinate The same procedure was performed as described in Example 1, except for using succinic acid instead of c-hydrochloric acid in Step 10 to obtain the title compound (453 mg, 86%).

$^1$H-NMR (400 MHz, DMSO-d$^6$) δ 10.68 (br s, 1H), 7.36 (br s, 1H), 6.76 (s, 1H), 6.59 (2, 1H), 4.17 (q, J=6.9, 7.3 Hz, 2H), 3.59~3.56 (m, 4H), 3.42 (s, 2H), 3.34~3.31 (m, 4H), 2.41 (s, 8H), 2.35 (br s, 4H), 1.75~1.72 (m, 2H), 1.40 (t, J=6.8 Hz, 3H)

Example 16

Preparation of 10-ethoxy-8-(morpholinomethyl)-1,2,3,4-tetrahydrobenzo[h][1,6]naphthyridine-5(6H)-on formate The same procedure was performed as described in Example 1, except for using formic acid instead of c-hydrochloric acid in Step 10 to obtain the title compound (427 mg, 94%).

$^1$H-NMR (400 MHz, DMSO-d$^6$) δ 10.69 (br s, 1H), 8.13 (s, 1H), 7.36 (br s, 1H), 6.76 (s, 1H), 6.59 (s, 1H), 4.17 (q, J=6.8, 7.2 Hz, 2H), 3.59~3.56 (m, 4H), 3.42 (s, 2H), 3.32~3.30 (m, 2H), 2.49~2.35 (m, 6H), 1.75~1.73 (m, 2H), 1.40 (t, J=6.9 Hz, 3H)

Example 17

Preparation of 10-ethoxy-8-(morpholinomethyl)-1,2,3,4-tetrahydrobenzo[h][1,6]naphthyridine-5(6H)-on glutamate The same procedure was performed as described in Example 1, except for using glutamic acid instead of c-hydrochloric acid in Step 10 to obtain the title compound (545 mg, 96%).

$^1$H-NMR (400 MHz, DMSO-d$^6$) δ 10.68 (br s, 1H), 7.36 (br s, 1H), 6.76 (s, 1H), 6.59 (s, 1H), 4.17 (q, J=6.9, 7.2 Hz, 2H), 3.59~3.52 (m, 4H), 3.41~3.27 (m, 8H), 2.42~2.34 (m, 6H), 1.87~1.81 (m, 1H), 1.75~1.72 (m, 2H), 1.40 (t, J=6.9 Hz, 3H)

Example 18

Preparation of 10-ethoxy-8-(morpholinomethyl)-1,2,3,4-tetrahydrobenzo[h][1,6]naphthyridine-5(6H)-on diphosphate The same procedure was performed as described in Example 1, except for using diphosphoric acid instead of c-hydrochloric acid in Step 10 to obtain the title compound (785 mg, 99%).

$^1$H-NMR (400 MHz, DMSO-d$^6$) δ 10.80 (s, 1H), 7.38 (s, 1H), 6.77 (s, 1H), 6.62 (s, 1H), 4.17 (q, J=6.8 Hz, 2H), 3.59 (m, 4H), 3.48 (s, 2H), 3.31 (m, 2H), 2.42 (m, 6H), 1.75 (m, 2H), 1.41 (t, J=6.8 Hz, 3H).

Comparative Example 1

Preparation of 10-ethoxy-8-(morpholinomethyl)-1,2,3,4-tetrahydrobenzo[h][1,6]naphthyridine-5(6H)-on dichloride anhydride 10-ethoxy-8-(morpholinomethyl)-1,2,3,4-tetrahydrobenzo[h][1,6]naphthyridine-5(6H)-on dichloride dihydrate prepared in Example 1 (3.0 g, 6.63 mmol) and 15.0 g of phosphorus pentoxide (P$_2$O$_5$) were put in a vacuum oven (Daihan Labtech, LVO-2060) and dried at 100° C., under 10 mmHg for 5 hours to obtain the title compound.

Comparative Example 2

Preparation of Amorphous 10-ethoxy-8-(morpholinomethyl)-1,2,3,4-tetrahydrobenzo[h][1,6]naphthyridine-5(6H)-on dichloride 10-ethoxy-8-(morpholinomethyl)-1,2,3,4-tetrahydrobenzo[h][1,6]naphthyridine-5(6H)-on dichloride dihydrate prepared in Example 1 (3.0 g, 6.63 mmol) was dissolved in 30 ml of distilled water and freeze dried. Then, the product thus obtained and 15.0 g of phosphorus pentoxide (P$_2$O$_5$) were put in a vacuum oven (Daihan Labtech, LVO-2060) and re-dried at 100° C., under 10 mmHg for 5 hours to obtain the title compound.

Experimental Example 1

Comparison of Stability of 10-ethoxy-8-(morpholinomethyl)-1,2,3,4-tetrahydrobenzo[h][1,6]naphthyridine-5(6H)-on dichloride dihydrate and 10-ethoxy-8-(morpholinomethyl)-1,2,3,4-tetrahydrobenzo[h][1,6]naphthyridine-5(6H)-on dichloride anhydride To compare the stability of 10-ethoxy-8-(morpholinomethyl)-1,2,3,4-tetrahydrobenzo[h][1,6]naphthyridine-5(6H)-on dichloride dihydrate prepared in Example 1 and 10-ethoxy-8-(morpholinomethyl)-1,2,3,4-tetrahydrobenzo[h][1,6]naphthyridine-5(6H)-on dichloride anhydride prepared in Comparative Example 1, the following experiment was performed.

3.0 g of each of the compounds was put in a Petri dish, and the Petri dish was left in a thermo-hygrostat maintaining 25° C. and 60% RH with an opened state. The moisture content with respect to time was measured using a Karl Fisher apparatus and recorded. By measuring the change of the moisture content with respect to time under the above-described conditions, the stability of the dihydrate and that of the anhydride were compared. The results are illustrated in the following Table 1 and FIG. 1.

TABLE 1

| | Moisture content of dihydrate of Example 1 (%) | Moisture content of anhydride of Comparative Example 1 (%) |
|---|---|---|
| Initial state | 8.77 | 0.40 |
| 30 min | 8.75 | 9.70 |
| 1 h | 8.80 | 10.18 |
| 2 h | 8.79 | 9.79 |
| 1 day | 8.77 | 9.72 |
| 2 days | 8.81 | 9.86 |

Figure 1:
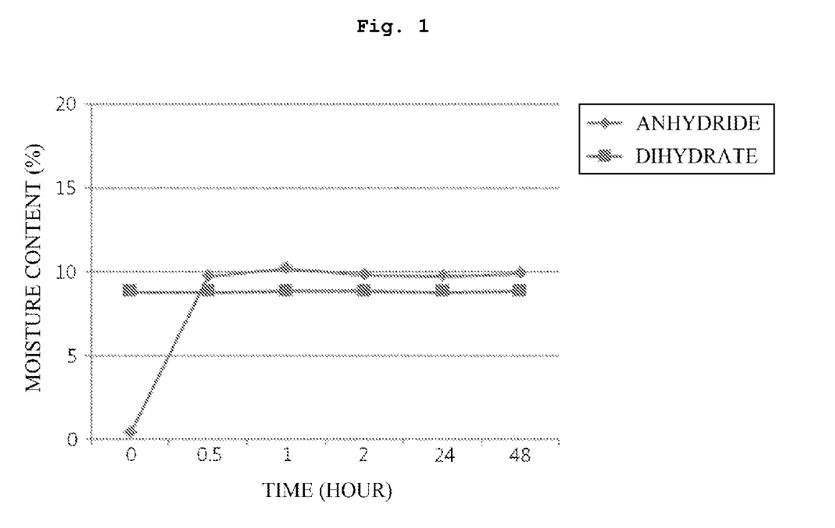
FIG. 1 illustrates moisture content of a dichloride dihydrate according to Example 1 of the present invention and an anhydride according to Comparative Example 1.

As shown in Table 1, from the measured results of the stability of the dihydrate of Example 1 according to the present invention and the anhydride of Comparative Example 1, the moisture content of the compound of Comparative Example 1 increased within 30 minutes from the initial state and absorbs moisture in the air. Thus, the compound of Comparative Example 1 rapidly changes into a crystalline type and is unstable. However, the moisture content of the compound according to the present invention is constant, and the compound is stable with respect to moisture and consequently stable with respect to hygroscopicity and so is very useful in maintaining quality when producing a drug. In addition, the compound according to the invention may be usefully used in a pharmaceutical composition for treating neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity.

Experimental Example 2

Comparison of Stability of Amorphous 10-ethoxy-8-(morpholinomethyl)-1,2,3,4-tetrahydrobenzo[h][1,6]naphthyridine-5(6H)-on dichloride For comparing the stability of the crystalline compound of Example 1 according to the present invention and the amorphous compound of Comparative Example 2, the following experiment was performed.

The stability of each of the crystalline compound of Example 1 according to the present invention and the amorphous compound of Comparative Example 2 was measured by measuring the change of a diffraction pattern through X-ray diffraction analysis (XRD).

Figure 2:
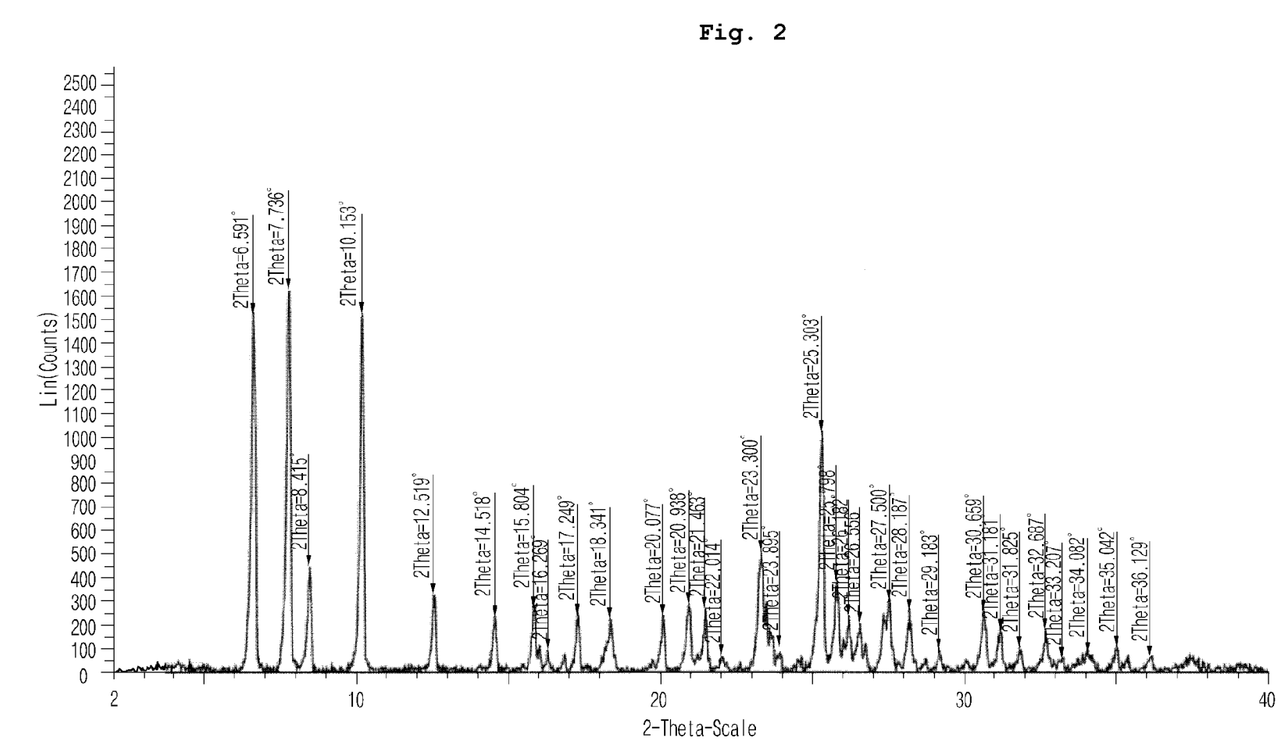
FIG. 2 illustrates XRD data of a dichloride dihydrate according to Example 1 of the present invention.
Figure 3:
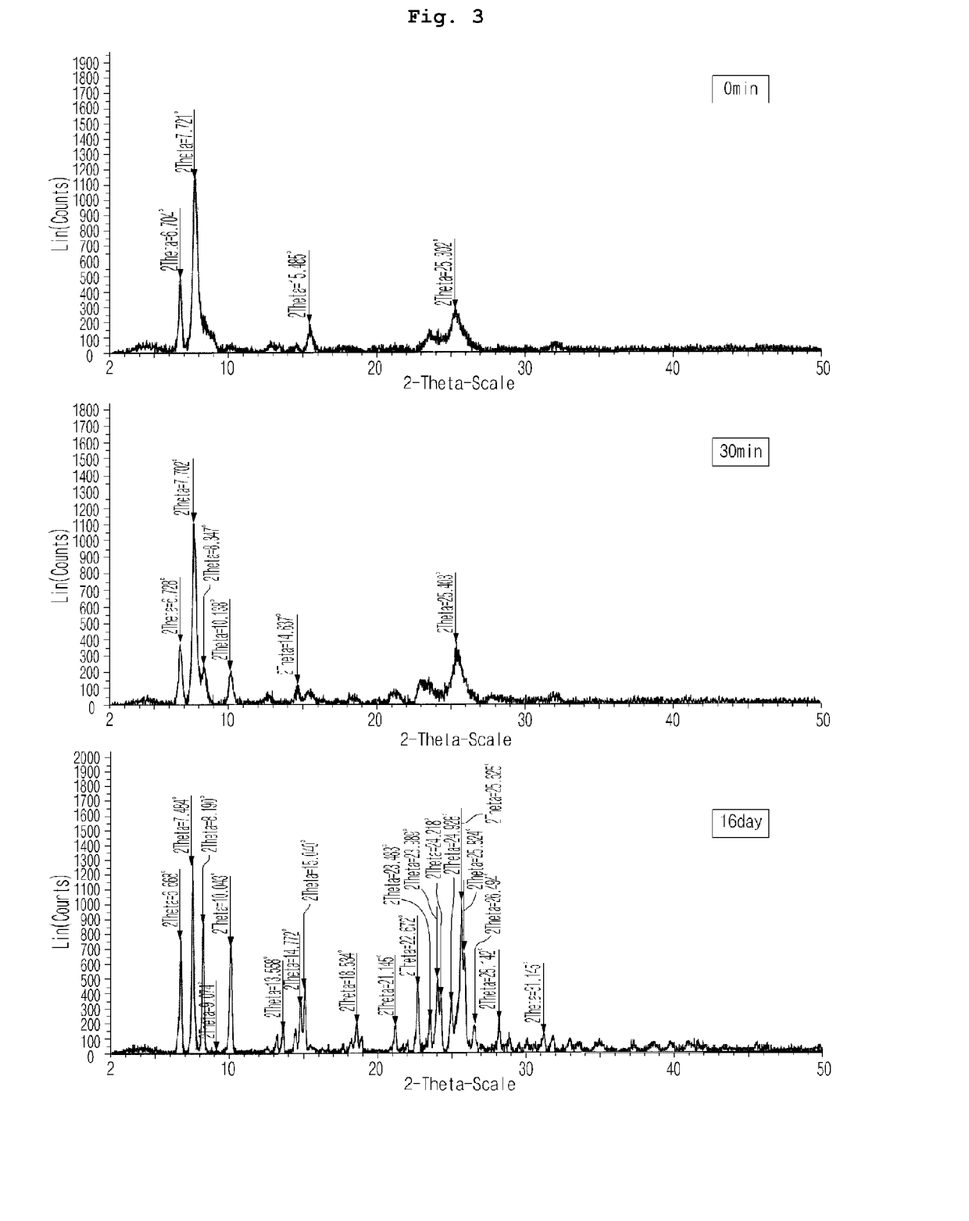
FIG. 3 illustrates the XRD peak change of an amorphous compound according to Comparative Example 2 with respect to time.

As a result, as shown in FIG. 2, constant data without change of the XRD diffraction pattern with respect to time were obtained for the crystalline compound of Example 1 according to the present invention. For the amorphous compound of Comparative Example 2, accurate and specific XRD pattern of the amorphous type was not shown, however amorphous 10-ethoxy-8-(morpholinomethyl)-1,2,3,4-tetrahydrobenzo[h][1,6]naphthyridine-5(6H)-on dichloride obtained after freeze drying absorbs surrounding moisture during performing the XRD, thereby increasing the crystallinity and showing XRD peaks. Thus, the compound of Comparative Example 2 was considered to absorb surrounding moisture, and the crystallinity thereof is increased (See FIG. 3).

For reference, 2θ values obtained by measuring XRD of a dichloride dihydrate of the compound of Chemical Formula 2 according to Example 1 are summarized and illustrated in the following Table 2.

TABLE 2

| Peak No | 2θ | d | I/I$_0$ |
|---|---|---|---|
| 1 | 6.59 | 13.40 | 94.0 |
| 2 | 7.74 | 11.42 | 100.0 |
| 3 | 8.42 | 10.50 | 27.4 |
| 4 | 10.15 | 8.71 | 93.9 |
| 5 | 12.52 | 7.06 | 19.6 |
| 6 | 14.52 | 6.10 | 14.0 |
| 7 | 15.80 | 5.60 | 16.5 |
| 8 | 16.27 | 5.44 | 4.9 |
| 9 | 17.25 | 5.14 | 14.7 |
| 10 | 18.34 | 4.83 | 13.3 |
| 11 | 20.08 | 4.42 | 13.9 |
| 12 | 20.94 | 4.24 | 17.1 |
| 13 | 21.46 | 4.14 | 15.7 |
| 14 | 22.01 | 4.03 | 3.7 |
| 15 | 23.30 | 3.81 | 30.8 |
| 16 | 23.90 | 3.72 | 6.1 |
| 17 | 25.30 | 3.52 | 62.4 |
| 18 | 25.80 | 3.45 | 22.6 |
| 19 | 26.18 | 3.40 | 14.0 |
| 20 | 26.56 | 3.35 | 12.0 |
| 21 | 27.50 | 3.24 | 17.9 |
| 22 | 28.19 | 3.16 | 15.4 |
| 23 | 29.18 | 3.06 | 5.2 |
| 24 | 30.66 | 2.91 | 15.2 |
| 25 | 31.18 | 2.87 | 10.5 |
| 26 | 31.83 | 2.81 | 6.2 |
| 27 | 32.69 | 2.74 | 10.4 |
| 28 | 33.21 | 2.70 | 3.2 |
| 29 | 34.08 | 2.63 | 5.0 |
| 30 | 35.04 | 2.56 | 6.3 |
| 31 | 36.13 | 2.48 | 3.8 |

Meanwhile, the moisture content of the compound of Comparative Example 2 was 0.4% immediately after drying, and was increased to 5.2% after measuring XRD.

Therefore, the compound according to the present invention is stable with respect to hygroscopicity and so is very useful in maintaining quality when producing a drug. In addition, the compound according to the invention may be usefully used in a pharmaceutical composition for treating neuropathic pain, epilepsy, stroke, Alzheimer's disease, Parkinson's disease, amyotrophic lateral sclerosis (ALS), Huntington's disease, schizophrenia, chronic and acute pain, ischemic brain injury, neuronal loss after hypoxia, trauma and nerve damage, which are medical conditions induced by PARP overactivity.

Experimental Example 3

Evaluating Yield Rate of Crystalline Compound According to Mixing Ratio of Mixed Solvent (Water+Organic Solvent) in Process of Second Recrystallization Crystalline compound of Example 1-18 according to the present invention has a characteristic feature of obtaining crystalline compound through adding organic acid to the compound "10-ethoxy-8-(morpholinomethyl)-1,2,3,4-tetrahydrobenzo[h][1,6]naphthyridine-5(6H)-on" in an organic solvent, then preparing acid-added salt with an organic solvent through first recrystallization, and then second recrystallizing the above prepared acid-added salt with water and organic solvent mixed solvent.

For measuring the change of crystalline compound yield rate according to mixing ratio of water and organic solvent in mixed solvent of the above second recrystallization, following experiment was performed.

In detail, yield rate of crystalline compound obtained through second recrystallization of 300 mg of acid-added salt "10-ethoxy-8-(morpholinomethyl)-1,2,3,4-tetrahydrobenzo[h][1,6]naphthyridine-5(6H)-on dichloride", which is obtained through identical performance of the first recrystallization process stated in Step 11 of Example 1, with 9.0 mL of mixed solvent prepared by changing mixing ratio (volumetric ratio) of water and acetone 1:1-20, was evaluated and shown in Table 3 below.

TABLE 3

| No. | Water:Acetone (volumetric ratio) | Yield Rate (%) |
|---|---|---|
| 1 | 1:1 | 0 |
| 2 | 1:2 | 0 |
| 3 | 1:3 | 0 |
| 4 | 1:4 | 60.6 |
| 5 | 1:5 | 68.0 |
| 6 | 1:6 | 82.5 |
| 7 | 1:7 | 82.9 |
| 8 | 1:8 | 89.3 |
| 9 | 1:9 | 89.4 |
| 10 | 1:10 | 90.3 |
| 11 | 1:20 | 91.7 |

As shown in Table 3, 1:4-20 of mixing ratios (volumetric ratio) of water and organic solvent can be used in mixed solvent used in the process of second recrystallization. Desirable ratios would be 1:8-10, and the most desirable ratio when considering the aspect of productivity and environmental circumstances would be 1:8.

The invention claimed is:

1. A crystalline acid salt of a tricyclic derivative represented by the following Chemical Formula 2:

2. The crystalline acid salt as set forth in claim 1, which shows specific peaks represented by 2θ in an X-ray diffraction pattern of Cu target radiation at 6.59°, 7.74°, 8.42°, 10.15°, 12.52°, 23.30°, and 25.30°.

3. A production method of the crystalline acid salt according to claim 1, the method comprising:
adding a hydrochloric acid in a tricyclic derivative of following Chemical Formula 1A in water or an organic solvent, performing a reaction completing the reaction, and first recrystallizing using an organic solvent (Step 1); and
recrystallizing the solid obtained in Step 1 using water and an organic solvent (Step 2), as shown in the following Reaction Formula 1:

[Reaction Formula 1]

Wherein n is 2, m is 2, and X is HCl.

4. A pharmaceutical composition comprising the crystalline acid salt according to claim 1, and a pharmaceutically acceptable carrier, for treating diseases induced by PARP (poly(ADP-ribose)polymerase) overactivity.

* * * * *